United States Patent [19]

Albrecht et al.

[11] 4,432,250
[45] Feb. 21, 1984

[54] HOTWELL SAMPLING SYSTEM

[75] Inventors: Leland J. Albrecht, Marlborough; Richard L. Briere, Hopkinton, both of Mass.

[73] Assignee: High Voltage Engineering Corporation, Burlington, Mass.

[21] Appl. No.: 395,330

[22] Filed: Jul. 6, 1982

[51] Int. Cl.³ .............................................. G01N 1/14
[52] U.S. Cl. .............................. 73/864.34; 73/61.1 R; 73/863.83
[58] Field of Search ...................... 73/864.34, 53, 60.1, 73/61 R, 61.1 R, 61.1 C, 61.2, 61.3, 61.4, 63, 64.1, 863.83, 864.81; 417/540

[56] References Cited

U.S. PATENT DOCUMENTS

| | | | |
|---|---|---|---|
| 3,451,895 | 6/1969 | Webb | 73/61.1 R |
| 3,796,089 | 3/1974 | Schuster et al. | 73/61.1 R |
| 4,024,061 | 5/1977 | Gatiss | 417/540 |
| 4,132,511 | 1/1979 | Boehme et al. | 417/540 |
| 4,245,963 | 1/1981 | Hutchins et al. | 417/540 |

Primary Examiner—Donald O. Woodiel
Attorney, Agent, or Firm—Henry C. Nields; Thomas J. Engellenner

[57] ABSTRACT

An apparatus and method for sampling condensate from a vacuum chamber employing a positive displacement pump, a pulsation dampener having sufficient volumetric flexibility to substantially dampen the pump's pressure surge, and a pressure regulating valve. The apparatus can be used in conjunction with sodium detectors, ion exchange analyzers, conductivity cells and other contaminant monitoring devices.

14 Claims, 4 Drawing Figures

HOTWELL SAMPLING SYSTEM

TECHNICAL FIELD

This invention relates to monitoring equipment for steam electric generating stations and, particularly, to an apparatus and method for sampling steam condensate from power plant condenser hotwells.

BACKGROUND OF THE INVENTION

The large majority of electric generating stations in the United States rely on steam production to generate electricity. Water is pressurized and boiled to produce superheated steam which expands its energy in mechanical work by driving a turbine; a dynamo connected to the turbine simultaneously produces electric power. It is crucial to the economic operation of the plant that the boiler feedwater and steam be kept essentially free of impurities. Contaminants such as air and other gases can alter fluid pH and otherwise greatly increase corrosion potential. Moreover, the ingress of solid contaminants such as sulphates, chlorides, phosphates, nitrates and other dissolved or volatile salts will promote excessive corrosion and scaling of boiler tubes, turbine blades and other exposed components.

One conventional method for detecting contaminants in steam is to sample the steam as it flows through a pipe. A multi-port sampling nozzle is inserted through the pipe wall, preferably extending across the entire diameter of the pipe. A sample is extracted, cooled and condensed for subsequent analysis. This method is fraught with difficulties and therefore not widely used.

In many ways it would be preferable to extract a sample of the steam condensate, continuously, if practicable, from the plant's condenser. (Typically, steam leaving a generating station's turbines is cooled and condensed in a barometric well or vacuum chamber called a condenser or more simply, a "hotwell"). Sampling from the hotwell would allow for a more reliable indication of the level of contaminants which have passed through the plant's entire water-steam cycle and would especially reflect contaminant levels from the turbine (i.e. oils and metals) and the condenser's cooling water tubes (i.e. coolant leakage). Hotwell sampling would be especially useful where sea water is used as the condenser coolant since in leakage of this high salt medium could accelerate corrosion throughout the power plant unless, of course, the leak is promptly detected and corrected.

Heretofore, there has not been effective apparatus for extracting to atmospheric pressure either a continuous or occasional "grab sample" from a hotwell. Since the phase change from steam to water in the condenser creates a vacuum which thereby reduces back pressure on the turbine, the act of sampling from the hotwell must also overcome the vacuum condition while not introducing air into the condenser.

Some power plant operators have devised ad-hoc systems for sampling their hotwells. The systems with which we are familiar have involved a large circulating pump (i.e. 10 gallons per minute) constantly pumping condensate from the hotwell and back into the hotwell. A portion of the return flow is restricted and, when sufficient back pressure is built up, a sample may be bled off. A major problem with such systems has been that the pumps are cumbersome and require considerable attention. Typically, the large pumps depend upon the circulatory water itself for cooling the armature and if the pump prime should be lost, due to power load swings or plant shut down for example, the pump motor may quickly burn out.

Others have tried to sample hotwells by complicated valving systems to isolate a portion of the condensate, bring it to atmospheric pressure and drain a grab sample. These systems have required manual operation and have not been able to provide continuous, on-line sampling capacity. Thus, another problem in sampling hotwell condensate is that an accurate volume of sample must be delivered to the analyzing instruments on a continuing basis without pressure surges that would damage the testing components or cause eroneous readings. There exists a need for a simple, robust sampler which can accomplish this challenging task and also provide related monitoring and testing functions. We are not aware of any commercially available sampler capable of providing this hotwell sampling function.

SUMMARY OF THE INVENTION

We have discovered that an effective hotwell sampling apparatus can be made with a simple metering pump and a pulsation dampener. In one aspect of our invention, back pressure is overcome using an electrically-driven piston or diaphragm-type pump. Preferably the displacement volume of the pump stroke is variable or set to a desired sample size or an integral fraction thereof. In another aspect of our invention, the inherent pulsation of a positive displacement-type pump can be dampened by a shock absorbing means. Our preferred shock absorber comprises a cannister packed with a flexible, closed-cell material, and connected directly to the discharge outlet of the pump. The packing may take the form of a coil or other configuration, the important design parameters being that the packing have sufficient volume to dampen the surge of the pump and that the material does not become water-logged. Preferable, the pulsation dampener is mounted vertically above the pump discharge and directly downstream of it.

Our sampler may be used in conjunction with various analyzing components, such as conductivity testers, ion-exchange analyzers and sodium detectors. For purposes of illustration our sampling system will now be described in connection with the following figures; however, it should be noted that various changes and modifications can be made by those skilled in the art without departing from the spirit and scope of our invention.

DETAILED DESCRIPTION OF THE PREFERRED EMBODIMENT

Figure 1:
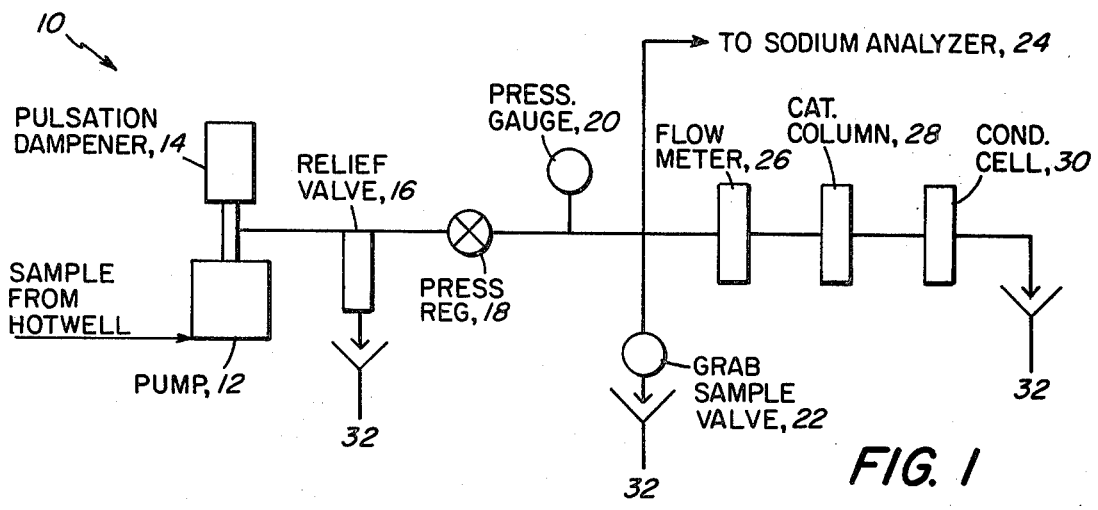
FIG. 1 is a schematic view of our invention showing the sample fluid path in block diagram form.

In FIG. 1 our sampling system 10 is shown comprising a positive displacement pump 12 (Liquid Metronics, Inc. Model B73); connected directly to the hotwell (not shown), a pulsation dampener 14 and analyzers 24–30. In our preferred embodiment the pump was modified to increase the strength of the piston return spring. Valve 22 permits a grab sample to be removed for off-line tests. The on-line analyzers include a sodium analyzer 24, which may be a flame photometer to detect low concentrations ($\approx 1$ ppb) sodium, a flow meter 26, an ion exchange analyzer 28 and a conductivity cell 30. Typically, ion analyzer 28 collects all the ionized dissolved solids on cation resins which are subsequently leached for chemical tests. The conductivity cell 30 may test the concentrated leachate or a portion of the sample itself. Flow meter 26 insures proper calibration of the ion analyzer 28 and conductivity cell 30. Pressure regulator 18 permits the analyzers to operate at atmospheric pressure and pressure gauge 20 is an indicator of operating conditions in the analyzer lines. In order to protect against malfunctions in the pulsation dampener 14 and to guard against pressure build up should the pump discharge more sample than can be handled by the analyzers 24-30, a relief valve 16 (50 psi) is installed upstream of regulator 18.

Figure 2B:
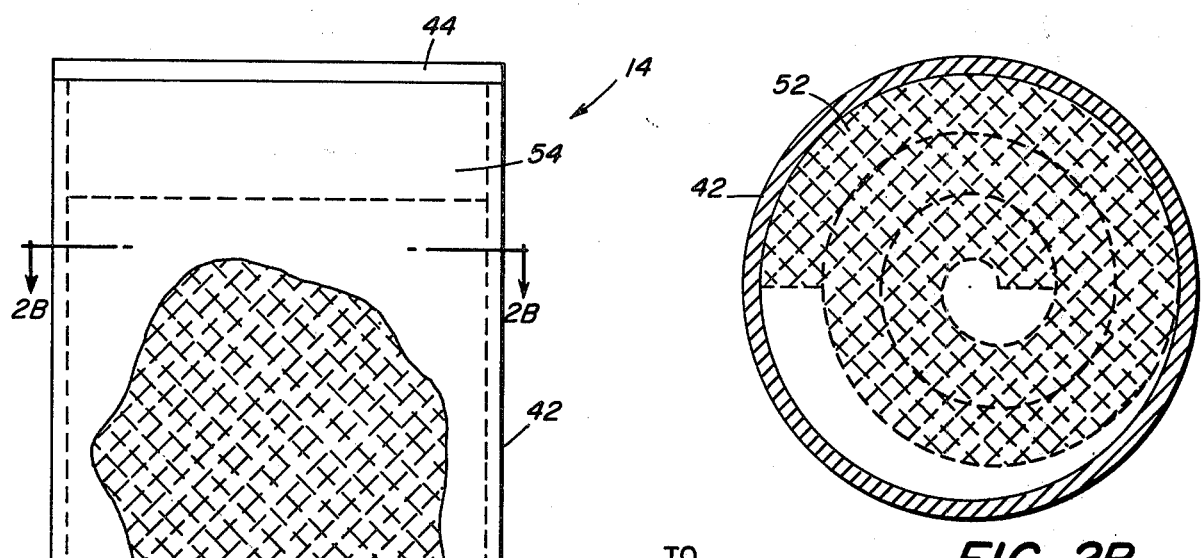
FIGS. 2a and 2b are a cross-sectional side view and top view of our pulsation dampener, respectively.
Figure 2A:
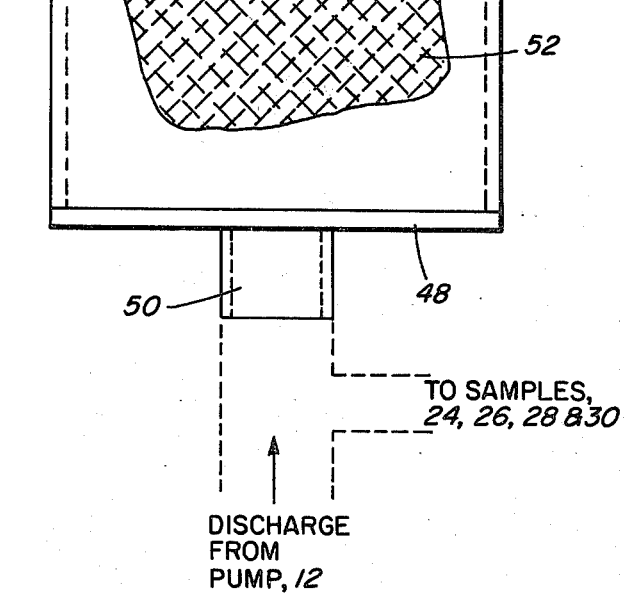

FIGS. 2a and 2b show the construction of our pulse dampener 14, which is formed from a cylindric element 42 (2.5 inch stainless steel pipe), top plate 44, bottom plate 48 (both also stainless steel) and coupling pipe 50 (0.25 inch NPT). As shown by the dotted lines, our dampener is preferably mounted vertically above the discharge outlet of pump 12 in fluid connection with the pump 12 and the downstream analyzers 24-30. Within dampener 14 is a coiled, flexible, closed-cell material 52 (i.e. Armaflex, a closed cell urethane foam manufactured by the Armstrong Cork Company of Lancaster, Pennsylvania.) In our embodiment the material 52 filled about four-fifths (4/5) of the dampener 14 with an open chamber 54 situated at the top of the dampener 14.

Figure 3:
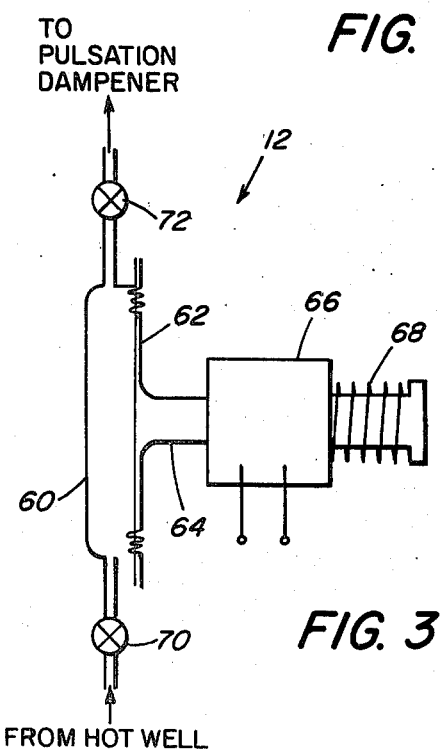
FIG. 3 is a schematic view of the pump of FIG. 1.

FIG. 3 shows a positive displacement pump 12 which may be used in our system 10. The pump 12 comprises a chamber 60, a diaphragm 62, piston 64, solenoid coil 66 and return spring 68. The chamber 60 has a mechanically activated entrance valve 70 and exit valve 72.

Initially, solenoid 66 is activated drawing piston 64 to the right in FIG. 3. Piston 64 draws diaphragm 62 to the right with it creating suction in chamber 60. The suction overcomes the force of gravity on valve 70 and permits chamber 60 to fill with water. Solenoid 66 is then deactivated and piston 64 returns by action of spring 68. The pressure of the piston 64 acting upon diaphragm 62 causes valve 70 to close and valve 72 to open permitting a sample to exit. (Valves 70 and 72 may be ball-and-seat valves or the like). The process is continued for as long as sampling is necessary.

Overall, the system operates as follows: A sample is withdrawn from the hotwell by displacement pump 12 and, after the sample has been dampened by dampener 14, it is passed through pressure regulator 18 to analyzers 24-30. Effluent from the analyzers as well as unused grab samples from valve 22 and excesses from relief valve 16 are discharged to drain 32.

Equivalents

A wide-variety of pumps may be employed in our sampling system; for example, small volume metering pumps, chemical feed pumps, diaphragm pumps, piston pumps, positive displacement pumps, and electrically and non-electrically driven pumps may all be employed. The important criteria is that the pump, if it is a reciprocating stroke pump, should be coupled to a dampener capable of dampening the surge of the displaced sample volume. Pulsation dampeners of various materials and configurations can be employed. While closed-cell packings are preferred, the range of equivalents should include any material capable of yielding volume in response to pressure surges (care should be taken in avoiding materials that can release trapped or dissolved air to the sample). Various analyzers may be employed in our sampling system to detect specific ions, gases, conductivity, purity or quality, in general, of the condensate.

Industrial Applications

Our invention should find application whenever there is a need to sample fluids under vacuum or low-pressure conditions in industrial or utility operations.

We claim:
1. An apparatus for on-line sampling condensate from a vacuum chamber comprising:
   (a) a positive-displacement pump, having an inlet in fluid connection with the condensate and an outlet discharging a volume of condensate per pump stroke;
   (b) a pulsation dampener in fluid connection with the pump outlet; and
   (c) a means for extracting the condensate discharged by the pump, said means being located downstream of both the pump and the dampener.
2. The apparatus of claim 1 wherein the pulsation dampener further comprises a dampener having a volume and composition such that for a given volume of condensate discharged by the pump, the dampener has sufficient volumetric flexibility to substantially dampen the pressure surge.
3. The apparatus of claim 2 wherein the pulsation dampener further comprises a sealed cannister substantially filled with a flexible, closed-cell material.
4. The apparatus of claim 1 wherein the pulsation dampener is mounted substantially vertically above the pump outlet.
5. The apparatus of claim 1 wherein the condensate extracting means further comprises a pressure-regulating valve.
6. The apparatus of claim 5 wherein the apparatus further comprises a relief valve for discharging excess condensate and relieving pressure.
7. A pulsation dampener for use in the apparatus of claim 1 comprising a sealed cannister substantially filled with a flexible, closed-cell, foam.
8. A steam condensate analyzing system comprising:
   (a) the apparatus of claim 1; and
   (b) at least one on-line analyzing component in fluid-connection with the means for extracting samples.
9. The system of claim 8 wherein the analyzing components comprise a sodium detector.
10. The system of claim 8 wherein the analyzing components comprise an ion exchange column.
11. The system of claim 8 wherein the analyzing components comprise a conductivity cell.
12. The system of claim 8 wherein the system further comprises a valve for off-line grab sample testing in fluid connection with the means for extracting samples.
13. A steam condensate analyzing system for testing condensate from a power plant hotwell comprising:
   (a) positive displacement pump, having an inlet in fluid connection with the condensate and an outlet discharging a volume of condensate per pump stroke;
   (b) a pulsation dampener in fluid connection with the pump outlet, said dampener comprising a sealed cannister substantially filled with a flexible, closed-cell material having sufficient volumetric flexibility to substantially dampen the pressure surge of the pump stroke and said dampener being mounted substantially vertically above the pump outlet;

(c) a pressure-regulating valve located downstream of both the pump and dampener for extracting the condensate discharged by the pump;

(d) A relief valve situated between the pump and the regulating valve for discharging excess condensate and relieving pressure; and (e) a least one, on-line, analyzing component in fluid connection with the regulating valve, whereby steam condensate from the hotwell may be extracted and tested for contaminants.

14. A method of sampling and testing steam condensate from a vacuum chamber, comprising:

(a) pumping out a volume of condensate from below the liquid level of the chamber without introducing gas or other contaminants into the chamber;

(b) dampening the pressure surge associated with the pumping against a vacuum;

(c) extracting the surge-dampened volume of condensate; and (d) analyzing the volume for contaminants.

* * * * *